United States Patent [19]
Gachet et al.

[11] Patent Number: 5,627,910
[45] Date of Patent: May 6, 1997

[54] PROCESS FOR INSPECTING METALLIC CHIPS FRAGMENTS IN ORDER TO ELIMINATE MORE X-RAY ABSORBENT INCLUSIONS FROM THEM

[75] Inventors: Maurice Gachet, Mercury; Thierry Ancillon, Albertville, both of France

[73] Assignee: Compagnie Europeenne Du Zirconium Cezus, Courbevoie, France

[21] Appl. No.: 266,709

[22] Filed: Jun. 28, 1994

[30] Foreign Application Priority Data

Jun. 30, 1993 [FR] France ................... 93 08229

[51] Int. Cl.$^6$ ..................................................... G06K 9/46
[52] U.S. Cl. ............................ 382/144; 382/155; 348/91
[58] Field of Search ........................... 209/576, 577, 209/588, 589, 938; 382/141, 152, 155, 160, 130, 144, 145, 274, 275; 348/86, 91, 92; 356/432, 433, 436, 437, 438, 439

[56] References Cited

U.S. PATENT DOCUMENTS

| | | | |
|---|---|---|---|
| 3,917,947 | 11/1975 | Fenton | 250/360 |
| 3,956,629 | 5/1976 | Gomm et al. | 250/223 R |
| 4,047,421 | 9/1977 | Spiers et al. | 73/1 R |
| 4,363,722 | 12/1982 | Dresty, Jr. | 209/3 |
| 4,854,977 | 8/1989 | Alheritiere et al. | 148/12.7 |
| 4,878,966 | 11/1989 | Alheritiere et al. | 148/421 |
| 5,202,932 | 4/1993 | Cambier et al. | 382/8 |
| 5,353,356 | 10/1994 | Waugh et al. | 382/8 |

FOREIGN PATENT DOCUMENTS

| | | |
|---|---|---|
| 514293 | 2/1982 | European Pat. Off. . |
| 2214294 | 8/1989 | United Kingdom . |

*Primary Examiner*—Leo Boudreau
*Assistant Examiner*—Larry J. Prikockis
*Attorney, Agent, or Firm*—Dennison, Meserole, Pollack & Scheiner

[57] ABSTRACT

The invention is a process for inspecting chips and/or fragments of metal or metal alloy to eliminate from them inclusions of a more X-ray absorbent material than the metal or alloy, wherein a field that delimits a portion of these chips and/or fragments is X-rayed. The process produces an X-ray image which is then converted into an electronic image. This image is analyzed in order to detect the inclusion(s) having features. The features include a background correction of the degree of illumination of each pixel in the field in the absence of chips and/or fragments, a field is covered with the portion of chips and/or fragments, and the electronic image is corrected by subtracting the background correction from the degree of illumination of each of its pixels, and the portion of chips and/or fragments is rejected if this corrected image contains at least one relative pixel corresponding to a chosen condition. Accordingly, the invention may be applied to recycling processes for metal or alloys in the fabrication of dependable parts.

12 Claims, 4 Drawing Sheets

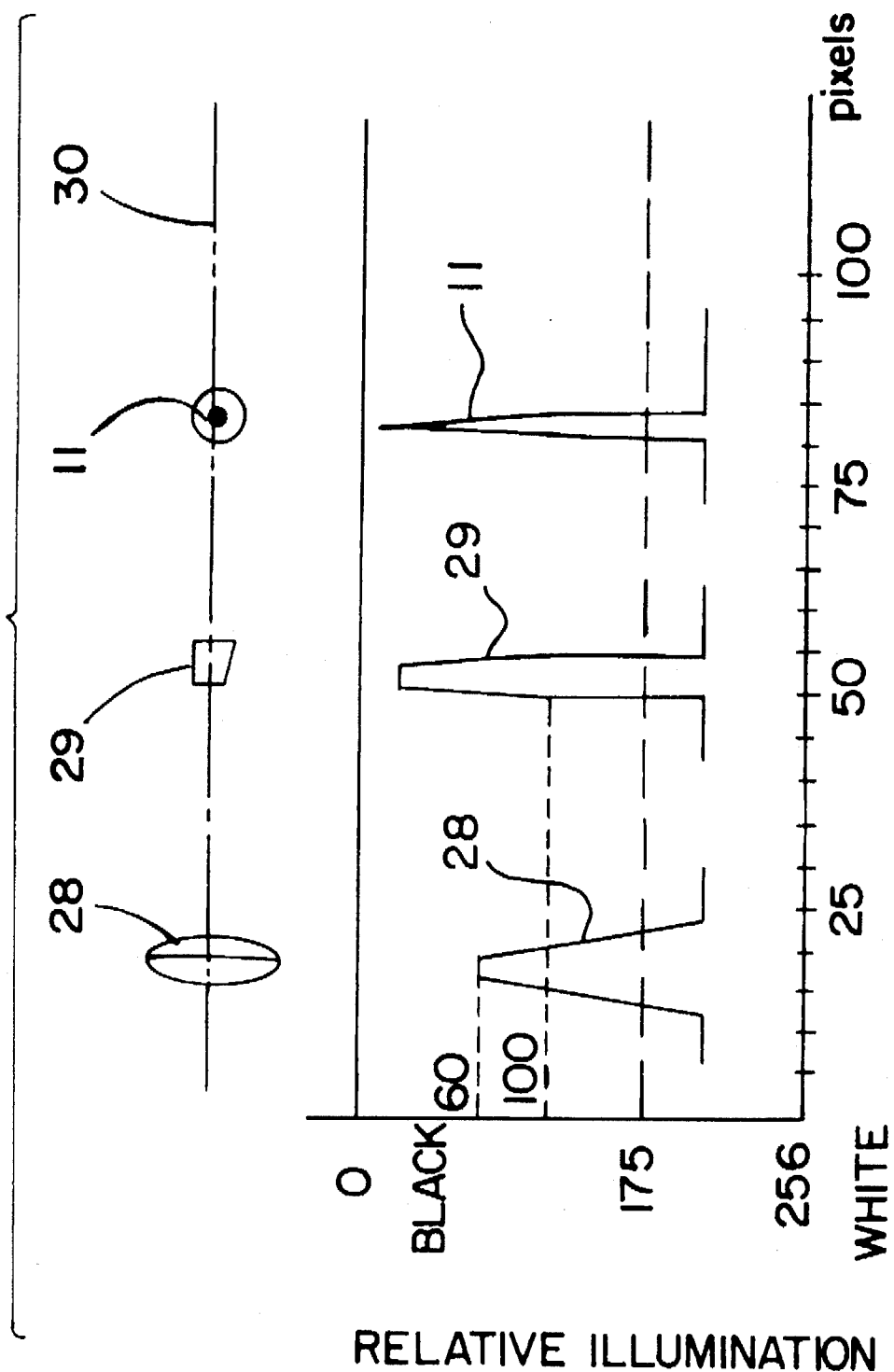

PROCESS FOR INSPECTING METALLIC CHIPS FRAGMENTS IN ORDER TO ELIMINATE MORE X-RAY ABSORBENT INCLUSIONS FROM THEM

FIELD OF THE INVENTION

The present invention relates to a process for inspecting chips or fragments of metal or metal alloy to eliminate any inclusions that are more X-ray absorbent than the metal or alloy, in accordance with which a field that delimits a portion of these chips or fragments is X-rayed, thus producing an x-ray image. This image is converted into an electronically transformed image which is analyzed in order to detect the inclusion(s) of more absorbent material present in the portion.

BACKGROUND OF THE INVENTION

Such a process is known from French patent FR-B-2 497 234 (equivalent U.S. Pat. No. 4,363,722), which is applied to wastes from the machining of titanium that have been pre-treated by pneumatic and magnetic separations, in order to detect any suspiciously high density inclusions therein. The wastes can be moved along in a continuous stream, with the X-rays passing through this stream and being detected by a sensor whose output signal is interpreted by a computer. Each part of the stream that contains a suspicious object that has been detected in this way is automatically removed and discarded. The accepted wastes may contain particles of high density material, for example tungsten carbide (hereinafter WC) WC, that are smaller than 0.38 mm or another specified value.

In the practice, globules of WC with a diameter of less than 0.38 mm and randomly cast into the X-rayed field are used as defect-measuring standards. The inventors determined that their detection was irregular and uncertain, and that the wastes accepted by the inspection process would contain, in places, inclusions that were "unacceptable" in principle, that is of high density and larger than 0.38 mm.

The inventors have taken on the task of improving the reliability, and if possible the sensitivity, of this X-ray inspection.

OBJECT AND SUMMARY OF THE INVENTION

An object of the invention is to define a correction of the background of coloration of each pixel in the field of the electronic image in the absence of any chips or fragments, wherein this correction originates from one or more X-rays of this field without any chips or fragments in it.

A further object of the, invention is to cover the field with said portion of chips or fragments, and the electronic image of the covered field is corrected by subtracting the background correction from the relative illumination ("degree of illumination") of each pixel of this image, thus producing a corrected image.

A still further object of this invention is to reject the portion of chips or fragments if the corrected image contains at least one doubtful pixel with an illumination corresponding to a chosen condition.

Further objects as well as advantages of the invention will become apparent from a consideration of the drawings and ensuing description.

Utilization of the background correction defined previously creates a uniformity in image that originates from the transmission of the X-rays through the empty background, a uniformity of the scale of the pixels, with each pixel typically having a colored surface of 0.01 mm$^2$, which produces a considerable improvement in the reliability and sensitivity of the detection of inclusions of more absorbent material than the chips or fragments, which are WC inclusions when these chips or fragments have been produced by machining with tungsten carbide tools.

The inventors determined that if during the check standard spherical globules of WC with a diameter of 0.38 mm, disposed sporadically in the X-ray field, were to be used during the inspection, in the related process they would be detected only in certain zones of the field but not in others, those which in fact corresponded to the darkest zones of the X-ray image of the empty background.

It must be noted that, in general,, the spherical standard globules with a diameter of 0.38 mm or less are typically detected by a low degree of illumination which appears as the darkening of a single pixel. A surface element that carries an elementary dot of color is called a "pixel".

With the invention, the previous drawback of irregular detection disappears, and the standard inclusions are detected at any point within the X-ray field. Reliability of the inspection is achieved, and these new conditions allow a greatly improved sensitivity of detection to be obtained. The degree of illumination of each pixel in the X-ray of the field in the absence of chips, or other fragments or scraps that is accounted for in the background correction of each X-ray image is preferably the average of the illuminations measured in several images, so as to do away with or at least reduce the incidence of aleatory phenomena. Even more preferably, an average of 4 to 16 successive images is made.

The assurance achieved by the inspection will reject the portion delimited by the field as soon as the corrected electronic image of this portion contains at least one "doubtful" pixel that is illuminated less than a chosen value. The term "doubtful" does not apply to the case of a black or dark gray pixel corresponding to a defect-measuring standard that can be located and then extracted from the portion under inspection.

The degrees of illumination of the pixels are numerical reference points in a scale of illumination of the X-ray image that proceeds, for example, from "0" for "black," which corresponds to the total blockage of X-rays by an absorbent body before the formation of the image, and a relatively high number, for example "256," for "white," which corresponds to a very good X-ray transmission.

If, then, the defect-measuring standard produces an illumination between 0 and 10, the value of the maximum degree of illumination of the "doubtful" pixels can be chosen from between 10 and 50, although other criteria can be involved in deciding if an inclusion must result in a rejection.

The expression "X-ray absorbent material" cannot, in its generality, be replaced by an expression that relates to specific mass. In fact, there can be exceptions to the practical rule according to which the absorption of X-rays increases with specific mass. The inventors have observed that a 1 mm thick sheet of Zircaloy 2, which is an alloy of about 98% Zr, is as X-ray absorbent as 2.5 mm of steel. The respective specific masses of Zr and Fe are 6.53 and 7.87. g/cm$^3$, while their respective atomic numbers are 40 and 26, rated in this case in inverse order from the increasing specific masses. Thus atomic structure, as well as specific mass, has an affect on the absorption of X-rays, and the indication of a material that is X-ray absorbent, or more X-ray absorbent, is more general than that of a "denser material."

Preferably, the maintenance of the precision of the inspection over time is assured by the sporadic random introduction of an X-ray absorbent defect-measuring standard into the field that is covered with the chips and/or fragments to be inspected. It is then verified that this defect-measuring standard is retrieved from the corrected image of the field, for not to retrieve it would result in the rejection of the portions inspected since the preceding introduction of the defect-measuring standard, and would bring the inspection to a stop while the device used before is readjusted for resumption of the inspection.

Equally preferably, in order to avoid blurs and attenuations in the variations of illumination at the very precise scale of the inspection, the chips and/or fragments are transported into the X-ray field by means of a conveyor belt. This portion of chips and/or fragments is then X-rayed once the belt is brought to a stop, with a overlaying of the successive x-rays of the portions.

In the case of the defect-measuring standards, it has been observed that their usually spherical, yet often in fact slightly oval, shape causes them to have unstable positions, even during the stop for X-raying.

In order to avoid this instability, each defect-measuring standard is preferably contained within a casing that is not, or not very, X-ray absorbent which has flat, stable supporting sides, for example a casing that is cubic on the outside. One supporting side is, for example, flat or concave with a flat outline. The control, over time, of the maintenance of the precision of the inspection is made reliable by this measure.

In order to further improve the sensitivity of the detection of X-ray absorbent inclusions, while at the same time having an effect on the sensitivity of the detection of defect-measuring standards, the X-ray image is preferably transformed into a corrected electronic image by performing, at least once, electronic filtering which enhances the contrasts in this electronic image.

This filtering is preferably effected by means of an operator with a table of N coefficients disposed on several successive lines, by placing this calculated table on N pixels and centering it on a specific pixel chosen from among these N pixels, with each of the N coefficients corresponding to one of the N pixels, and with the specific pixel being allocated to a new degree of illumination calculated as follows: the illumination of each pixel is multiplied by the corresponding coefficient, then the sum of the results of these multiplications is calculated and this sum is eventually divided by a number P greater than 1, thus obtaining a result, and the specific pixel is allocated to the degree of illumination that is equal to this result; and step by step the table is superseded by successively choosing each pixel of the image as a specific pixel and allocating this pixel to a new degree of illumination calculated by the preceding method. The eventual division by the number P is used to maintain the results at the scale of the degrees of illumination.

This filtering process accentuates the contrasts by modifying the degree of illumination of each pixel in relation to the illuminations of the pixels which surround it. This first filtration is preferably accompanied by the use of an illumination threshold, for example "175" for the scale of illumination already described as being from "0" (black) to "256": if there are no pixels with a degree of illumination less than this threshold, the portion is accepted; if there is at least one pixel with an illumination less than 175, that is to say darker, the batch is either rejected or detained for a complement of tests. In the latter case, the apparatus preferably delimits, within the image of the field that has once been corrected and filtered in this way, a narrower zone containing this or these darker pixels, so as to limit the duration of the complementary examination.

The inventors have tried several commercially available operators in order to effect this transformation which enhances the contrasts of the image. The known operator or "mask" (M1) produces the best results for improvement of the contrasts at the scale under consideration, that of the pixels which is described in the examples; its drawback is that it leads to a long processing time for all the pixels in an image of 50×75 mm (409600 pixels), approximately 3 seconds. It is desirable to greatly reduce this time for the series inspection while retaining an equally good enhancement of contrast. The inventors have designed a mask (M2) which produces an enhancement of contrasts that is at least as good as (M1), and with a more compact table of coefficients, which has a processing time of between 40 and 60 ms for all the pixels in the above image. The following represents this table, in which the specific point is in the central position (coefficient "10"):

| (M2) | | | | | | |
|---|---|---|---|---|---|---|
| 0 | −1 | −1 | −1 | −1 | −1 | 0 |
| 0 | 0 | 0 | 0 | 0 | 0 | 0 |
| −1 | −1 | 4 | 10 | 4 | −1 | −1 |
| 0 | 0 | 0 | 0 | 0 | 0 | 0 |
| 0 | −1 | −1 | −1 | −1 | −1 | 0 |

Preferably, the image projects slightly beyond the image of the portion under inspection so that the pixels of this image of the portion will be processed. A divisor P, for example equal to N, or 35, is often used with (M2).

For a portion whose electronic image, which has been corrected and processed to enhance contrasts for the first time, comprises one or more pixels with a degree of illumination lower than the chosen threshold, an examination is carried out:

either the diagnosis of unacceptable inclusion(s) is clear and these inclusions are either selectively extracted, or the entire portion is rejected;

or there is some doubt and any zone of the image which contains any doubtful pixels is made to undergo at least one new processing, and then a complementary examination.

Generally, for an electronic image which has, depending on the dimensions and the intermeshing of the pixels, between 200,000 and 600,000 pixels, the mask (M2) designed by the invention permits processing of the entire image to be accomplished in less than 80 ms.

The definitive diagnosis typically takes into account the morphology of the chips and fragments and also the morphology of the inclusions of more absorbent matter. The inventor has noted that the inclusions that are very X-ray absorbent and small in size, WC inclusions for example, locally exhibit maximum darkening and a fringe with a degree of illumination that rapidly increases from this maximum darkening. It is the very abrupt character of this variation in illumination which distinguishes, for example, the image of a WC inclusion and that of a chip of a fragment that has been beveled by machine.

Thus, the inspected portion, or the part of this portion corresponding to the zone of the image that has undergone processing and a complementary examination, is rejected if its corrected electronic image comprises degrees of illumination which vary locally and rapidly along a line of pixels, these illuminations so varying according to a multiplying coefficient between 2 and 5 for a distance of 0.05 to 0.5 mm along the line. For the application of this rule, the preferred scale of degrees of illumination has a zero corresponding to black and a chosen number between 100 and 500, for example "256," for white.

The process of the invention applies particularly to chips and/or fragments of titanium or titanium alloy, consisting of at least 65% by mass of titanium, which will be cast into ingots for the fabrication of aircraft parts. The dependability requirements are therefore great; the most common alloy is Ti-Al 6%-V 4% (% by mass), and the most high-performance alloys are specifically described in French Patent FR-B-2 614 040 (equivalent EP 287 486 and U.S. Pat. No. 4,854,977) and U.S. Pat. No. 4,878,966 and in French Patent application FR-A-2 676 460 (equivalent EP 514 293).

Proper application of the process of the invention leads in general to absolutely surprising assurances of the absence of more X-ray absorbent inclusions: typically far less than 0.5 mg of inclusions, such as WC inclusions, per 100 kg of chips and/or scrap. This assurance can be brought to less than 0.2 mg, and even better, less than 0.13 mg, per 100 kg, as will be described in the examples.

Returning to Ti and its alloys, the defect-measuring standards which are used for adjusting the sensitivity and the points of comparison are preferably spherical globules with a diameter that is less than those that are known, which have a diameter of 0.38 mm, typically a diameter of between 0.15 and 0.3 mm. The utilization of easily detected WC globules with a diameter of 0.25 mm, which have a unitary mass of 0.128 mg, and which are preferably enclosed in a casing with flat support surfaces, is a considerable improvement over the prior utilization of globules with a diameter of 0.38 mm and a unitary mass of 0.45 mg, the detection of which was irregular and uncertain.

In order to have a constant sensitivity as well as a reasonable efficiency of inspection for the inspection of the portion of chips and/or scraps., it is desirable to maintain the surface mass of the chips and scraps of Ti or alloy between 25 and 60 g per $cm^2$ of the field of inspection. If the chips are constantly of the same type, this mass can be maintained at a chosen value of + or −5 $g/cm^2$, thus allowing a very finely regulated inspection following assured detection of measuring-standard globules with a diameter such as 0.25 mm or 0.2 by a single pixel.

The invention has the following advantages:

A background correction of the image of the portion of chips and/or fragments, which provides excellent reliability and an increase in the sensitivity of the inspection.

Stability of the defect-measuring standards equipped with a casing with a flat, stable supporting side, which makes the control, over time, of the maintenance of the precision of the inspection reliable.

A procedure for enhancing the contrasts of the electronic image, which allows for industrial recognition of very small inclusions.

Assurance of the absence of inclusions at a level of less than 0.5 mg of inclusion per 100 kg, which simplifies recycling by allowing direct recycling without any intermediate melting to control.

BRIEF DESCRIPTION OF THE DRAWINGS

FIG. 5 shows the X-rayed elements as seen from below and the corresponding degrees of illumination in their images.

DESCRIPTION OF THE INVENTION

Figure 1:
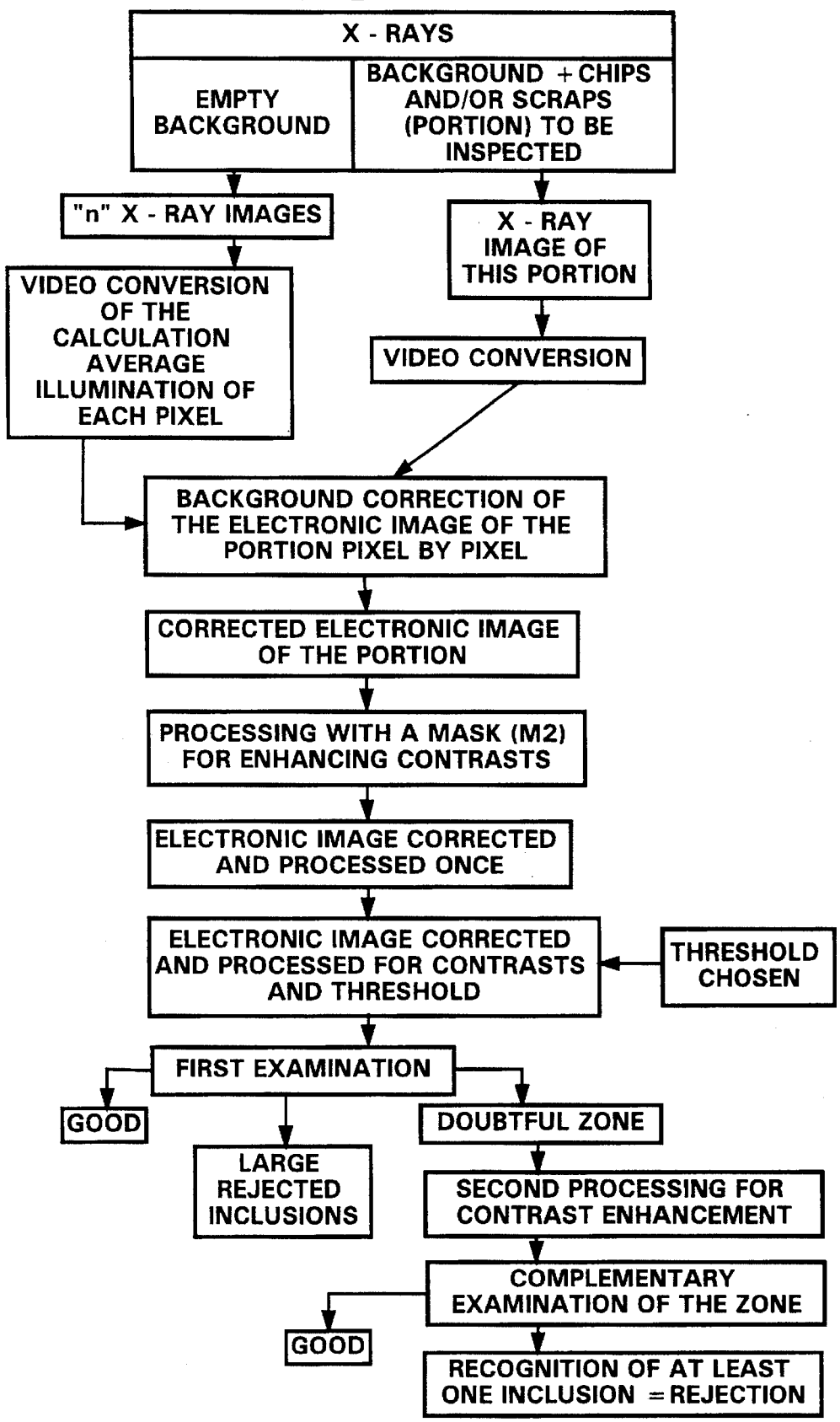
FIG. 1 is a diagram of the successive operations of the process and the successive states of the image of the inspected portion.

1. Device Used (FIG. 2:) in the Execution of the Process (FIG. 1).

Figure 2:
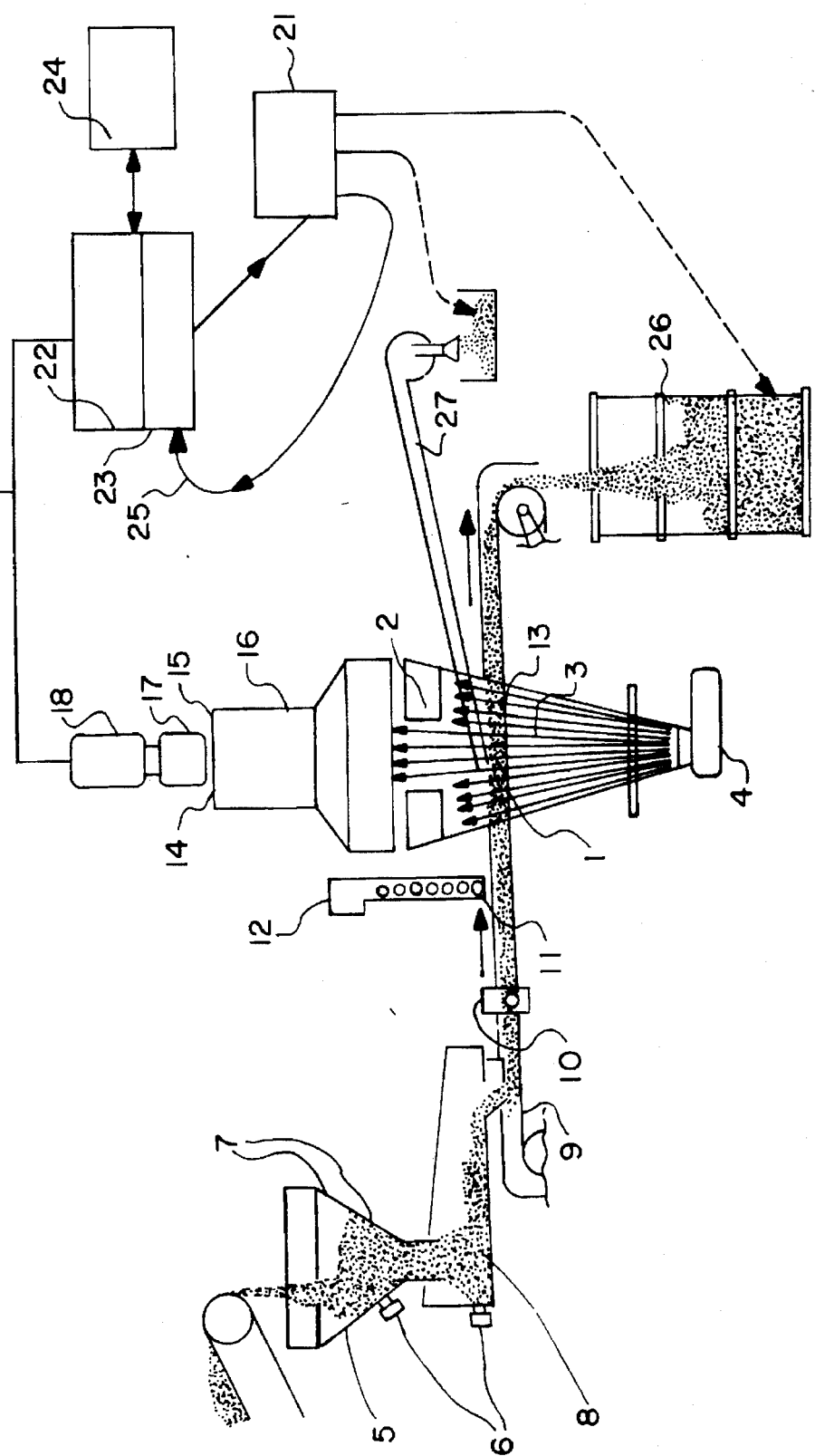
FIG. 2 shows a device used in the execution of the process of the invention.

The device in FIG. 2 is used, in particular, to inspect chips and fragments of titanium alloy Ti- Al 6%-V4% that have resulted from machining by tools with cutting edges of tungsten carbide WC. Its function is to assure the accepted product a residual content of WC inclusions that is less than 0.5 mg per 100 kg.

The device has means for bringing the chips and fragments into the X-ray field 1, which is defined by a window 2 through which pass 160 kV X-rays 3 issuing from a generator 4.

FIG. 2 delineates a hopper 5 equipped with vibrating means 6 and level detectors 7, and shows the chips and fragments 8 passing along a conveyor belt 9 into which a thin strip of copper or lead has preferably been incorporated that is absorbent of very low-energy X-rays. Carried along by this belt 9, the chips and fragments 8 are sized to a chosen total thickness of 20 mm by a regulation means 10. Then, before reaching the field 1 and being held up there by a stoppage of the belt 9, the chips and fragments 8 sporadically receive a WC measuring-standard globule 11 that is delivered to a random position by a distributor 12.

The measuring-standard globules such as 11 have a diameter of 0.25 mm and are each encased in a cube of plastic of 10 mm to a side, which assures their stability during the formation of the X-ray image and facilitates their extraction and manipulation afterward.

X-rays such as 3 which have passed through either the empty belt 9, or the belt 9 and the portion 13 of chips and fragments 8 with a surface mass of 45 $g/cm^2$ which have been held within the field 1, are converted into an X-ray image 14 on a screen 15 by means of a photo-cathode 16. This image 14 is then transformed into an electronic image by a lens 17 and a video camera 18. Also, it can potentially be displayed just as it is on a screen 20.

This electronic image is then processed by at least a "background correction" of each pixel, which removes variations in uniformity in the background that corresponds to the image being studied. Thus four successive images of the background (the belt 9 itself) are taken, the sum of the degrees of illumination of each pixel in these four images is divided by 4, and the average illumination achieved by each pixel is subtracted from its degree of illumination in the electronic image of the inspected portion 13.

In this example, the corrected image that has been obtained is treated immediately afterward to a contrast enhancement relative to a threshold, or minimum acceptable degree of illumination, of "175" in the 0–256 scale used here. After this correction and these processes, the corrected image is processed and examined on the screen 21 the moment it shows anything doubtful ("first examination").

FIG. 2 shows a part of the system 22 that effects the background correction, and a part 23 that effects the process of enhancing contrasts using the mask (M2) and the inspection in comparison to the chosen threshold, both of which communicate with a computer 24.

The field of inspection 1 is 50×75 mm. The successive electronic images, displayed at 20 and 21, have 512 lines of 800 pixels, or 409600 pixels of approximately 0.1×0.1 mm each.

When a doubtful zone appears on the screen 21, it is reprocessed (arrow 25) for enhancement of contrasts and inspected in comparison to the threshold in the part 23, then re-examined on the screen 21. This re-examination, like the first examination, can be conducted either upon acceptance, with the portion on the belt being brought by the belt to the receptacle 26 for good products (the broken arrow shows this action), or upon a total or partial rejection operated by an extraction system 27.

The processes for enhancing contrasts are executed with the mask (M2) described previously.

The diagram in FIG. 1 summarizes the successive operations that are carried out as well as the successive images such as have been outlined in the present description.

2. Assurances of Absence of Inclusions Obtained—Comparative Results.

Three factors are involved in the good results of the invention:

reliability of detection, due to the background correction;

the possibility of being guided by smaller defect-measuring standards;

assured recognition of the inclusions.

In the known technology, which uses WC measuring-standard globules with a diameter of 0.38 mm, it was found that 6% of these randomly distributed measuring-standard globules were not detected. Thus, it could not assure a maximum number of inclusions per 100 kg that would be less than the mass of 6 measuring-standard globules, or 2.7 mg of WC.

With the invention, there is an assurance of less than the mass of one WC defect-measuring standard in 100 kg of chips and/or scraps of titanium alloy, either less than 0.45 mg with globules that have a diameter of 0.38 mm, or less than 0.13 mg with globules that have a diameter of 0.25 mm.

Processing of the corrected image makes decisions more precise, and leads to rejecting less and improving the assurance.

3. Contrast-Enhancing Mask

A known enhancing mask was tested ("Mask 7," p. 14–5, SAPPHIRE Operator's Manual, ref. DRG 201596X–005 60/01/137Y, Ed. Quantel Ltd., UK, 1988: "A Mild Filter for Enhancing Slightly Diffuse Image Detail") which containing the following table of 7×7 coefficients:

| (M1) | | | | | | |
|---|---|---|---|---|---|---|
| 0 | 0 | 0 | −1 | 0 | 0 | 0 |
| 0 | −1 | −1 | −1 | −1 | −1 | 0 |
| 0 | −1 | 0 | 4 | 0 | −1 | 0 |
| −1 | −1 | 4 | 10 | 4 | −1 | −1 |
| 0 | −1 | 0 | 4 | 0 | −1 | 0 |
| 0 | −1 | −1 | −1 | −1 | −1 | 0 |
| 0 | 0 | 0 | −1 | 0 | 0 | 0 |

With an electronic image of 409600 pixels, this mask (M1) performs processing of the image in 3 seconds. With the reprocessing of zones, this length leads to slowing of the inspection.

The tests conducted by the inventor lead to the design of the mask (M2) with which the electronic image is treated at in less than 40 ms.

Figures 3, 4:
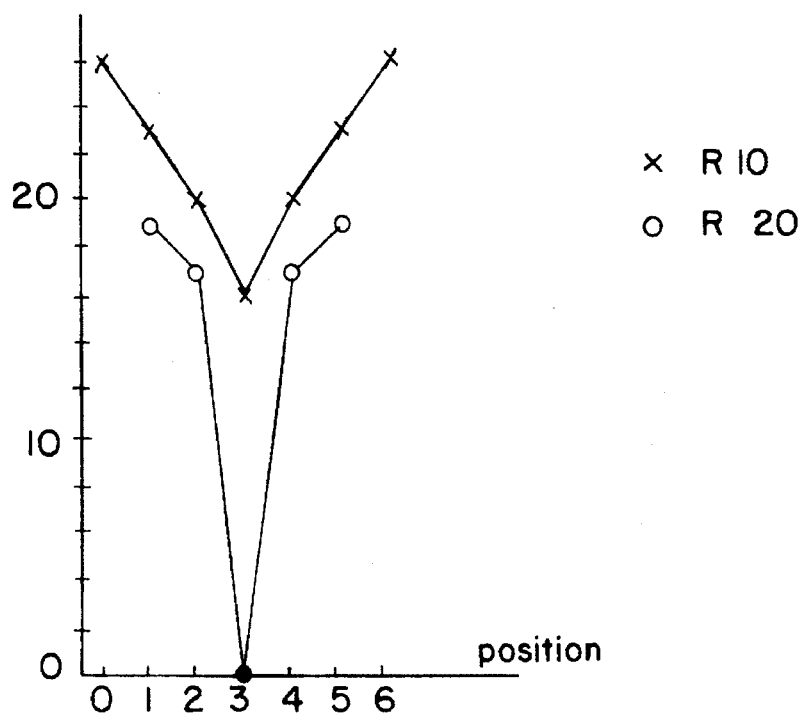
FIGS. 3 and 4 show the degrees of illumination of the pixels of an image before and after an electronic filtering to enhance the contrasts.

4. Example of Contrast Enhancement (FIG. 3)

This example, in principle, makes it possible to understand the effect of contrast enhancement that is brought about by an electronic mask such as (M1) or preferably (M2).

Table R1 shows a zone of an image 31 with 5×5 pixels surrounded by a border of pixels 32.

The table (M3) is that of an operator with 3×3 coefficients.

The application of this electronic operator or "mask" (M3) to the entire image 31 in order to enhance its contrasts leads to the image 33 in table R2.

| (M3) | | |
|---|---|---|
| 0 | −1 | 0 |
| −1 | 5 | −1 |
| 0 | −1 | 0 |

The line marked with arrows 34 connects the pixel on the left side of the first line of the image 31 to its transformation in the image 33, a pixel whose degree of illumination has passed from "28" to "34." The central pixel passes from dark gray "16" to black "0.". FIG. 4 summarizes the degrees of illumination of the pixels of the central line of the image prior to processing (line R10) and after processing (line R20) of the image by (M3): the contrast enhancement is substantial.

5. Recognition of Inclusions of Much More X-ray Absorbent Material than that of the Inspected Chips and/or Fragments.

In the present examples, chips and fragments of titanium alloy are considered, which have a specific mass of 4.5 and inclusions of WC, a material that is much more X-ray absorbent and has a specific mass of 15.63.

In general cases, aside from Zr and its alloy, the inspection process of the invention may be applied even more easily because the ratio of the specific masses of the materials that are present together is increased, and is preferably higher than 1.5. "More easily" typically refers to complementary examinations that are less frequent and less involved, that is to say requiring fewer complementary contrast enhancements. In a case where one of the materials is Zr or its alloy, the other material can be for example Ti or its alloy or V or its alloy, or Fe or steel, and it may be assumed that the ratio of the thicknesses of each of the materials that are present together which have similar X-ray absorption would be preferably higher than 1.5. Each material can also be replaced by a mixture of materials, provided that the ratios of X-ray absorption or of specific mass specified above would be retained between the chips and/or fragments on one hand and the inclusions on the other hand.

Returning to the case of the chips or fragments of Ti alloy and the inclusions of WC issuing from the cutting edges of machining tools, FIG. 5 shows a chip 28 of Ti alloy in a field, a WC inclusion 29, and a measuring-standard globule 11 with a diameter of 0.25, as seen from above, and below these it shows the degrees of illumination of their X-ray images 14 or their electronic images within a plane 30 which intersects the elements 28, 29, 11 and the line of the corresponding pixels, with the X- rays in this plane 30 being nearly vertical, as shown in FIG. 2.

The chip 28 has an S-shaped profile, and its center part stands on edge, which produces a degree of illumination of 60, that is to say a dark gray. Each edge produces a linear growth of this illumination up to about 200 in 0.7 mm. According to the special rule for the recognition of inclusions, (in which the degrees of illumination that vary according to a multiplying coefficient between 2 and 5 for a distance of 0.05 to 0.5 mm produce a rejection), the variation in the degree of illumination in the present case is too slight, and the chip 28 is not rejected as a defect.

The WC inclusion 29 produces at its center a degree of illumination of 15 in 3 pixels (0.3 mm), and on each edge a relative linear increase in illumination from 15 to 100 in 0.1 mm, followed by a rise to an illumination of approximately 200 for the batch of chips. Each of these relative increases, considered for example at half its value, satisfies the special rule. The inclusion 20 produces a rejection.

The measuring-standard globule 11 produces a maximum darkening of the degree of illumination of 5 in 0.1 mm (a single pixel) and an increase in the degree of illumination from 5 to 100 in 0.2 mm or from 5 to 25 in 0.05 mm. This increase just satisfies the special rule. The globule 11 is normally followed, marked and removed from the batch.

The inclusions with a mass equal to that of this measuring standard globule most often produce a degree of illumination that is less than 30 in at least 2 pixels. This observation can simplify the decisions.

The invention can be applied to solving problems with the recycling of metals or alloys in the fabrication of dependable parts.

What is claimed is:

1. A process for inspecting chips (8, 28) or fragments (8) of metal or metallic alloy in order to eliminate from them any inclusions (29) that are of a more X-ray absorbent material than said metal or alloy, wherein a field (1) which delimits a portion (13) of these chips (8, 28) or fragments (8) is X-rayed, thus producing an X-ray image (14), and this image (14) is converted into an electronic image which is analyzed for detecting said inclusion(s) (29) of more absorbent material that are present in said portion (13), said process comprising:

defining a background correction image for variations in the degree of illumination of each pixel in the field (1) of an electronic image in the absence of any chips (8, 28) and/or fragments (8), by electronically recording one or more-X-rays of the field (1) without any chips or fragments present;

covering the field (1) with said portion (13) of chips (8, 28) and/or fragments (8), generating an x-ray image of the covered field, converting the x-ray image into an electronic image and correcting the electronic image of said covered field (1) by subtracting said background correction image from the electronic image; and rejecting said portion (13) of chips (8, 28) and/or fragments (8) if said corrected electronic image contains at least one doubtful pixel with a degree of illumination corresponding to a chosen condition, making a plurality of sporadic and random introductions into said covered field (1) of an X-ray absorbent defect-measuring standard (11) contained in a casing that is X-ray pervious and has flat supporting sides;

verifying whether each introduction of said defect-measuring standard (11) is retrieved from the corrected image of said field (1); and if an introduction of said defect-measuring standard is not retrieved, rejecting the portions (13) inspected since a preceding introduction of said defect-measuring standard into said covered field was retrieved from the corrected image (11); and stopping the inspection while the process is adjusted for resumption of the inspection, thereby assuring maintenance of precision of said inspecting.

2. A process in accordance with claim 1, including the steps of:

transporting said chips (8, 28) and/or fragments (8) into said field (1) by means of a conveyor belt (9);

x-raying said portion (13) of chips (8, 28) and/or fragments (8) once the belt is brought to a stop, with an overlaying of the successive X-ray images of said portions (13).

3. A process in accordance with claim 1, comprising the further step of:

converting the X-ray image (14) into a corrected electronic image by performing, at least once, an electronic filtering to enhance the contrasts of said corrected electronic image.

4. A process in accordance with claim 3, wherein said step of filtering is effected by means of an operator with a table (Mr, M2) of N coefficients disposed on several successive lines, by placing said table on N pixels and centering it on a specific pixel chosen from among the N pixels, with each of the N coefficients corresponding to one of the N pixels, and with the specific pixel being allocated to a new degree of illumination;

multiplying the illumination of each of said N pixels by the corresponding coefficient to give a result, then calculating the sum of the results of said multiplications, and eventually dividing the sum by a number P greater than 1, thus obtaining a further result;

allocating the specific pixel to the degree of illumination that is equal to the further result; and superseding the table by successively choosing each pixel of the image as a specific pixel and allocating this pixel to a new degree of illumination calculated thereby.

5. A process in accordance with claim 4, wherein said operator has the following table (M2) of coefficients, with the specific pixel in the central position:

| 0  | −1 | −1 | −1 | −1 | −1 | 0  |
|----|----|----|----|----|----|----|
| 0  | 0  | 0  | 0  | 0  | 0  | 0  |
| −1 | −1 | 4  | 10 | 4  | −1 | −1 |
| 0  | 0  | 0  | 0  | 0  | 0  | 0  |
| 0  | −1 | −1 | −1 | −1 | −1 | 0. |

6. A process in accordance with claim 5, wherein said filtering is repeated for at least one zone of the corrected electronic image, this zone corresponding to a part of the portion (13) under inspection.

7. A process in accordance with claim 5, wherein, with said corrected electronic image having between 200,000 and 600,000 pixels, said filtering is effected in less than 80 ms.

8. A process in accordance with claim 7, wherein said portion (13) or part of the portion (13) of chips (8,28) and/or fragments (8) is rejected if its corrected electronic image varies in illumination along a line of pixels by a factor between 2 and 5 over a distance of 0.05 to 0.5 mm along said line.

9. A process in accordance with claim 8, wherein said chips (8, 28) and/or fragments (8) are titanium or an alloy containing at least 65% by mass of titanium.

10. A process in accordance with claim 1, wherein each defect-measuring standard (11) is a spherical globule of tungsten carbide with a diameter between 0.15 and 0.3 mm.

11. A process in accordance with claim 10, wherein the thickness of each portion (13) of chips (8, 29) and/or fragments (8) to be X-rayed is regulated in order to have 25 to 60 grams of the chips and/or fragments per $cm^2$ of said field (1).

12. A process in accordance with claim 10, wherein there is an assurance that less than 0.5 mg of tungsten carbide (29) per 100 kg of chips (8,28) and/or fragments (8) will be accepted (26).

* * * * *